US00PP37319P2

(12) United States Plant Patent
van Swieten

(10) Patent No.: US PP37,319 P2
(45) Date of Patent: Mar. 10, 2026

(54) ***PHALAENOPSIS* PLANT NAMED 'PHA569755'**

(50) Latin Name: *Phalaenopsis hybrida*
Varietal Denomination: PHA569755

(71) Applicant: ANTHURA B.V., Bleiswijk (NL)

(72) Inventor: Martinus Nicolaas Gerardus van Swieten, Utrecht (NL)

(73) Assignee: ANAMURA B.V., Bleiswijk (NL)

( * ) Notice: Subject to any disclaimer, the term of this patent is extended or adjusted under 35 U.S.C. 154(b) by 0 days.

(21) Appl. No.: 19/316,629

(22) Filed: Sep. 2, 2025

(51) Int. Cl.
*A01H 6/62* (2018.01)
*A01H 5/02* (2018.01)
*A01H 5/12* (2018.01)

(52) U.S. Cl.
USPC ..... Plt./311
CPC ..... *A01H 6/62* (2018.05); *A01H 5/02* (2013.01); *A01H 5/12* (2013.01)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'PHA569755', characterized by its upright plant habit; moderately vigorous growth habit and moderate growth rate; strong flowering stems; freely flowering habit with typically two tall inflorescences developing per plant, each inflorescence with numerous flowers; white-colored flowers with greenish yellow and white labella; and good postproduction longevity.

2 Drawing Sheets

Figure 1:
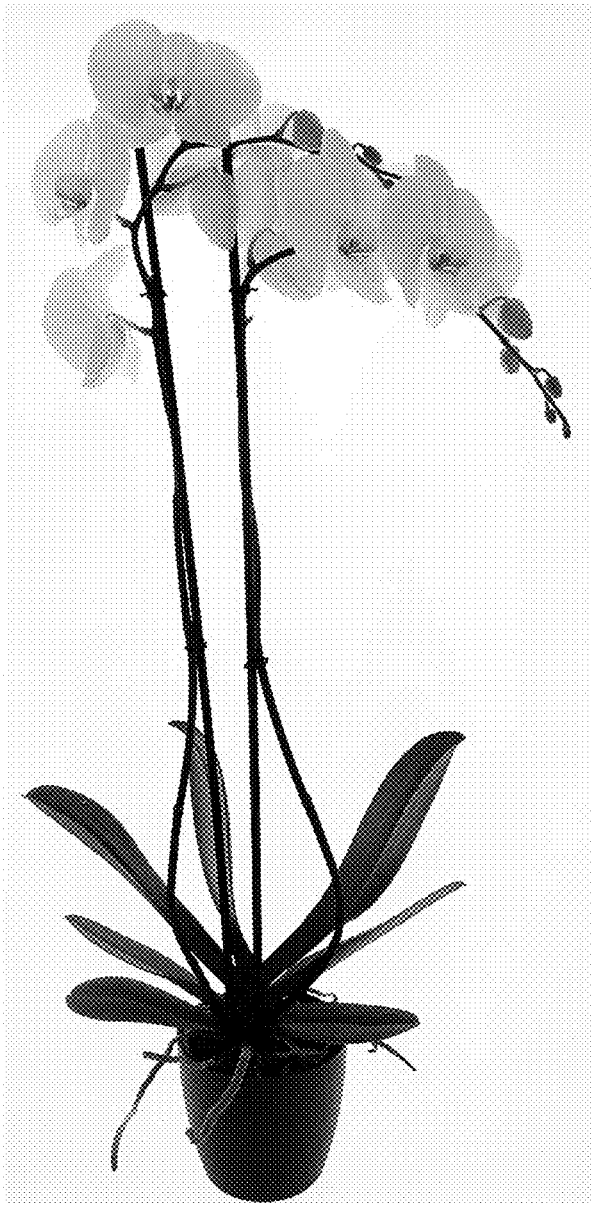

Botanical designation: *Phalaenopsis hybrida.*
Cultivar denomination: 'PHA569755'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Dec. 30, 2024, application number 2024/3259. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA569755'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique patterns and coloration.

The new *Phalaenopsis* plant originated from a cross-pollination in July, 2017 in Bleiswijk, The Netherlands of *Phalaenopsis hybrida* 'PHALGUZQEN', disclosed in U.S. Plant Pat. No. 33,119, as the female, or seed, parent with a proprietary breeding selection of *Phalaenopsis hybrida* identified as code number 14-060142-0001, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in April, 2020.

Asexual reproduction of the new *Phalaenopsis* plant by in vitro meristem propagation in a controlled environment in Bleiswijk, The Netherlands since April, 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA569755'. These characteristics in combination distinguish 'PHA569755' as a new and distinct *Phalaenopsis* plant:

1. Upright plant habit.
2. Moderately vigorous growth habit and moderate growth rate.
3. Strong flowering stems.
4. Freely flowering habit with typically two tall inflorescences developing per plant, each inflorescence with numerous flowers.
5. White-colored flowers with greenish yellow and white labella.
6. Good postproduction longevity.

Plants of the new *Phalaenopsis* can be compared to plants of the female parent, 'PHALGUZQEN'. Plants of the new *Phalaenopsis* differ primarily from plants of 'PHALGUZQEN' in the following characteristics:

1. Leaves of plants of the new *Phalaenopsis* are semi-erect in aspect whereas leaves of plants of 'PHALGUZQEN' are semi-erect to horizontal in aspect.
2. The leaf apices of plants of the new *Phalaenopsis* are emarginate whereas the leaf apices of plants of 'PHALGUZQEN' are not emarginate.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are semi-erect in aspect whereas leaves of plants of the male parent selection are horizontal in aspect.
2. The leaf apices of plants of the new *Phalaenopsis* are moderately asymmetric whereas the leaf apices of plants of the male parent selection are slightly asymmetric.

Plants of the new *Phalaenopsis* can be compared to plants of *Phalaenopsis hybrida* 'PHALFUBNE', disclosed in U.S. Plant Pat. No. 30,395. In side-by-side comparisons, plants of the new *Phalaenopsis* differ primarily from plants of 'PHALFUBNE' in the following characteristics:

1. Leaves of plants of the new *Phalaenopsis* are semi-erect in aspect whereas leaves of plants of 'PHALFUBNE' are erect to semi-erect in aspect.
2. Peduncles of plants of the new *Phalaenopsis* are moderately to strongly tinged with anthocyanin whereas peduncles of plants of 'PHALFUBNE' are slightly to moderately tinged with anthocyanin.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA569755' grown in a container.

Figure 2:
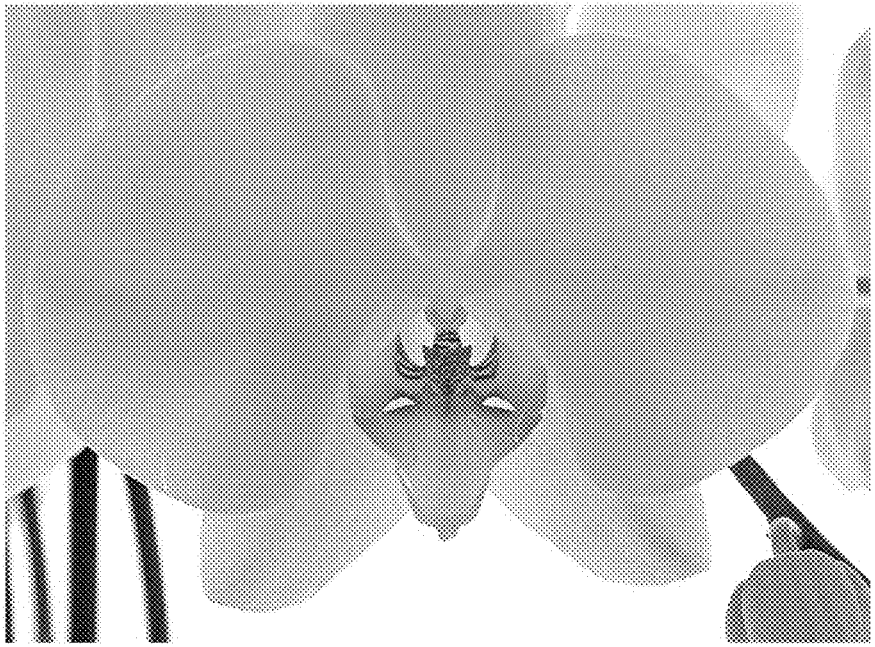

The photograph on the second sheet (FIG. 2) is a close-up view of a typical flower of 'PHA569755'.

DETAILED BOTANICAL DESCRIPTION

The aforementioned photographs and following observations and measurements describe plants grown during the winter in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA569755'.

Parentage:

*Female, or seed, parent.*—*Phalaenopsis hybrida* 'PHALGUZQEN', disclosed in U.S. Plant Pat. No. 33,119.

*Male, or pollen, parent.*—Proprietary breeding selection of *Phalaenopsis hybrida* identified as code number 14-060142-0001, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; dense.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 22.7 cm.

*Plant height, substrate level to top of floral plane.*—About 70.9 cm.

*Plant diameter or spread.*—About 31.4 cm.

Leaf description:

*Arrangement and quantity.*—Distichous, simple; sessile; about six to seven fully-developed leaves per plant.

*Length.*—About 22.8 cm.

*Width.*—About 8.6 cm.

*Aspect.*—Semi-erect.

*Shape.*—Obovate to obovate-oblong; slightly carinate.

*Apex.*—Emarginate, moderately asymmetric.

*Base.*—Sheathing. Sheath length: About 2.8 cm. Sheath width: About 1.6 cm. Sheath color: Close to 143C; towards the margins, close to 143A.

*Margin.*—Entire; not undulate.

*Texture and luster, upper surface.*—Smooth, glabrous; moderately glossy.

*Texture and luster, lower surface.*—Smooth, glabrous; slightly glossy.

*Venation pattern.*—Camptodromous.

*Color.*—Developing leaves, upper surface: Close to a blend of NN137A and 147A; narrow marginal edges, close to 145A. Developing leaves, lower surface: Close to a blend of 146A and 147A; narrow marginal edges, close to 145A. Fully expanded leaves, upper surface: Close to NN137A; narrow marginal edges, close to 144A; venation, close to a blend of 147A and N189A. Fully expanded leaves, lower surface: Close to a blend of 146A and 147B; narrow marginal edges, close to 144A; venation, close to 143A.

Inflorescence description:

*Appearance and flowering habit.*—Showy zygomorphic flowers arranged on axillary simple or branched racemes; typically two inflorescences develop per plant; each inflorescence with about eleven flowers; flowers face outwardly on upright to outwardly arching inflorescences supported by upright peduncles;

flowers with three petals, two lateral petals and one center petal transformed into a labellum and three sepals.

*Fragrance*.—None detected.

*Time to flower*.—Plants begin flowering about 4.5 months after planting; plants flower naturally during the winter into the spring.

*Flower longevity*.—Long flowering period, individual inflorescences maintain good substance for about 15 weeks on the plant; flowers not persistent.

*Inflorescence length* (*lowermost flower to inflorescence apex*).—About 31.8 cm.

*Inflorescence width*.—About 18.2 cm.

*Flower buds*.—Height: About 2.3 cm. Diameter: About 1.6 cm by 1.8 cm. Shape: Broadly ovate. Color: Close to 145B; towards the apex, tinged with close to 174C.

*Flower size*.—About 11.3 cm (vertical) by 12.6 cm (horizontal).

*Flower depth*.—About 3.7 cm.

*Petals, quantity and arrangement*.—Three, two lateral petals and one center petal transformed into a labellum.

*Lateral petals*.—Length: About 6 cm. Width: About 7.6 cm. Shape: Broadly reniform to close to broadly lunate. Apex: Obtuse. Margin: Entire; not undulate. Texture and luster, upper surface: Smooth, glabrous; velvety; matte. Texture and luster, lower surface: Smooth, glabrous; moderately velvety; matte. Color: When opening, upper surface: Close to NN155C to NN155D; towards the base, close to NN155A. When opening, lower surface: Close to NN155C; towards the base, close to 157C. Fully opened, upper and lower surfaces: Close to NN155D; color does not change with subsequent development.

*Labella*.—Appearance: Three-parted with two lateral lobes and a central lobe; overall shape, broadly cordate. Length, lateral lobes: About 2.5 cm. Width, lateral lobes: About 1.9 cm. Length, central lobe: About 2.4 cm. Width, central lobe: About 7 mm to 30 mm. Length, cirrhose tips: About 3.7 cm. Shape, lateral lobes: Obovate. Shape, central lobe: Deltoid with an elongated apex. Apex, lateral lobes: Obtuse. Apex, central lobe: Acute with two cirrhose apices, moderately curled and pointing upwards and backwards. Margins, lateral and central lobes: Entire. Texture and luster, lateral and central lobes, upper and lower surfaces: Smooth, glabrous; velvety; matte. Callosities: Located at the base of the labellum and attachment point of the lateral petals; about 6 mm in length, about 7 mm in width and about 6 mm in height. Color: When opening, upper surface: Lateral lobes: Close to NN155D; lower margins, close to 2B; at the base, axial stripes, close to 180C. Central lobe: Close to NN155D; towards the base, close to 154C and 154D; below callosities, close to 182C; at the base, close to 155C with radial stripes, close to 184B and 184C; cirrhose apices, close to NN155D and at the tip, close to 154C and 154D. Callosities: Close to 2B to 2D; at the apex, close to 5A with dense fine dots, close to 175C. When opening, lower surface: Lateral lobes: Close to NN155D; lower margins, close to 3B. Central lobe: Close to 155A and 154C; upper margins, close to 166B to 166D; at the base, close to 182D and 160D; cirrhose apices, close to 155A. Fully opened, upper surface: Lateral lobes: Close to NN155D; lower margins, close to 5B; at the base, axial stripes, close to 180B. Central lobe: Close to NN155D; towards the base, close to 1B; below callosities, close to 182B; at the base, close to 155C with radial stripes, close to 185B; cirrhose apices, close to NN155D and at the tip, close to 1B. Callosities: Close to 12D; at the apex, close to 14B with dense fine dots, close to 179A. Fully opened, lower surface: Lateral lobes: Close to NN155D; lower margins, close to 7B. Central lobe: Close to 155C and 5B; towards the apex, close to NN155D; upper margins, close to 166B to 166D; at the base, close to 186C, 186D and 156D; cirrhose apices, close to 155C.

*Sepals*.—Quantity and arrangement: Three, one upper dorsal sepal and two lower lateral sepals. Length, dorsal sepal: About 4.7 cm. Width, dorsal sepal: About 3.9 cm. Length, lateral sepals: About 4.7 cm. Width, lateral sepals: About 3.5 cm. Shape, dorsal sepal: Elliptic. Shape, lateral sepals: Ovate. Apex, dorsal sepal: Obtuse to shallow retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper surface: Smooth, glabrous; velvety; matte. Texture and luster, dorsal and lateral sepals, lower surface: Smooth, glabrous; moderately velvety; matte. Color, dorsal sepal: When opening, upper surface: Close to 155C. When opening, lower surface: Close to a blend of 145D and 150D slightly tinged with close to 186D; towards the margins, close to 155C. Fully opened, upper surface: Close to NN155D. Fully opened, lower surface: Close to NN155B slightly tinged with close to 186D; towards the apex and margins, close to NN155D. Color, lateral sepals: When opening, upper surface: Close to 155C; lower half, tinged with close to 157D; towards the base, close to 150C and 150D. When opening, lower surface: Close to 145D slightly tinged with close to 186D; towards the margins, close to a blend of 145D and 155C. Fully opened, upper surface: Close to a blend of 155C and NN155A; towards the upper margins, close to NN155C; at the base, close to 150D. Fully opened, lower surface: Close to a blend of 150D and 155C slightly tinged with close to 186D; towards the margins, close to NN155C.

*Peduncles*.—Length: About 81.8 cm. Diameter: About 6 mm. Strength: Strong. Aspect: Upright to outwardly arching. Texture and luster: Smooth, glabrous; matte. Color: Close to 200A with dense fine dots and marbling, close to 147C.

*Pedicels*.—Length: About 4.8 cm. Diameter: About 4 mm. Strength: Moderately strong. Aspect: About 65° from peduncle axis. Texture and luster: Smooth, glabrous; matte. Color: Close to 145D; distal end, close to N155B; proximal end, close to 148A.

*Reproductive organs*.—Androecium: Column length: About 1 cm. Column width: About 6 mm. Column color: Close to NN155C. Pollinia quantity: Two. Pollinia diameter (per two pollinia): About 3 mm. Pollinia color: Close to 24A. Gynoecium: Stigma length: About 3 mm. Stigma width: About 4 mm. Stigma shape: Reniform. Stigma color: Close to NN155C. Ovary length: About 1 cm. Ovary diameter: About 1 mm. Ovary color: Close to 150B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA569755' as herein illustrated and described.

* * * * *